(12) United States Patent
Kim et al.

(10) Patent No.: US 7,709,783 B2
(45) Date of Patent: May 4, 2010

(54) BIOSENSOR USING MULTIPLE LIGHT SOURCES

(75) Inventors: Mu-gyeom Kim, Hwaseong-si (KR);
Sang-yeol Kim, Gwacheon-si (KR);
Sung-hun Lee, Seoul (KR); Jung-bae Song, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 101 days.

(21) Appl. No.: 12/030,479

(22) Filed: Feb. 13, 2008

(65) Prior Publication Data
US 2008/0277604 A1 Nov. 13, 2008

(30) Foreign Application Priority Data
May 7, 2007 (KR) ...................... 10-2007-0044218

(51) Int. Cl.
*H01L 31/14* (2006.01)
(52) U.S. Cl. ..................... 250/221; 250/552; 250/458.1; 257/40; 422/82.05
(58) Field of Classification Search .............. 250/208.1, 250/221, 552, 553, 458.1; 257/40, 642, 759; 422/80.05, 82.08
See application file for complete search history.

(56) References Cited

U.S. PATENT DOCUMENTS 6,331,438 B1 \* 12/2001 Aylott et al. ................ 436/172

\* cited by examiner

*Primary Examiner*—Kevin Pyo
(74) *Attorney, Agent, or Firm*—Cantor Colburn LLP

(57) ABSTRACT

Provided is a biosensor that uses multiple organic light emitting diodes (OLEDs) as light sources. The biosensor includes a transparent substrate, a plurality of OLEDs which are disposed on a first surface of the transparent substrate and are electrically separated from each other, and a photo detector above the transparent substrate that receives light emitted from a specimen disposed on the transparent substrate, wherein the specimen is disposed on a region of a second surface which is a surface opposite to the first surface of the transparent substrate.

16 Claims, 3 Drawing Sheets

BIOSENSOR USING MULTIPLE LIGHT SOURCES

CROSS-REFERENCE TO RELATED PATENT APPLICATION

This application claims the benefit of Korean Patent Application No. 10-2007-0044218, filed on May 7, 2007, in the Korean Intellectual Property Office, the disclosure of which is incorporated herein in its entirety by reference.

BACKGROUND OF THE INVENTION

1. Field of the Invention

The present invention relates to a biosensor using multiple light sources, and more particularly, to a biosensor that uses a plurality of organic light emitting diodes as light sources.

2. Description of the Related Art

Biosensors or biological detecting systems convert information obtained from an object into recognizable signals such as colors, fluorescence, or electrical signals by using biological elements or by imitating biological elements.

Biosensors have been compactly designed to be easily used by users, and studies have been carried out to increase the sensitivity of the biosensors. In particular, there are many kinds of dyes which attach to a material to be detected to emit photo-luminance (PL) in a biosensor. However, there are limitations in actually using many kinds of dyes in the biosensor due to the limitation of spectrums generated by a light source which is a light emission unit. Accordingly, in a biological detecting system, a light source must be able to generate various spectrums to widen the selectivity of dyes.

FIG. 1 is a schematic drawing of a conventional biosensor. Referring to FIG. 1, after disposing a plurality of dyes 11 on a substrate 10, light emitted from a light source 13 is radiated onto a specimen (not shown), for example, a protein specimen dropped on the substrate 10. At this point, the dyes 11 generate PL by absorbing a portion of a light spectrum received from the light source 13, and a light receiving unit 15 or a photo detector detects the amount of PL received. An optical filter 17 is installed on the light receiving unit 15, and the optical filter 17 transmits the intensity of light with respect to PL having a predetermined wavelength.

In the conventional biosensor, a plurality of optical filters 17 are used in the light receiving unit 15. Thus, the structure of the light receiving unit 15 is complex, and the optical filters 17 reduce the intensity of light which results in the reduction of measuring sensitivity of the biosensor, and accordingly, in order to increase the intensity of light, the amount of a specimen must be increased. The increased number of optical filters 17 limits the selectivity of dyes 11, and thus, measurement with respect to various specimens is difficult. In addition, the increased number of optical filters 17 increases manufacturing cost of biosensors.

SUMMARY OF THE INVENTION

To address the above and/or other problems, the present invention provides a compact biosensor that includes a light receiving unit that does not use optical filters and a light source that can generate various spectrums, wherein in the biosensor, the light source and a specimen are adjacently disposed on a substrate.

The present invention also provides a biosensor that can detect an increased range of biological objects to be detected by increasing the number of light sources available.

According to an aspect of the present invention, there is provided a biosensor comprising: a transparent substrate; a plurality of organic light emitting diodes (OLEDs) which are disposed on a first surface of the transparent substrate and are electrically separated from each other; and a photo detector above the transparent substrate that receives light emitted from a specimen, wherein the specimen is disposed on a region of a second surface which is an opposite surface of the first surface of the transparent substrate.

The biosensor may further comprise a plurality of reflection films, each formed on a surface of each of the OLEDs not to face the transparent substrate.

The OLEDs may be formed in a single layer or in multiple layers formed of a material that emits red, green, or blue wavelength of light, respectively.

The material may have a spectrum having a full width at half maximum of 50 to 100 nm.

The OLEDs may be formed in a matrix arrangement.

Each of the OLEDs may have a shape of a segment of a circle to form a circle if the OLEDs get together.

The OLEDs may have a polygonal shape.

The biosensor may further comprise a sealing material to cover the OLEDs on the transparent substrate.

According to another aspect of the present invention, there is provided a biosensor comprising: a transparent first substrate; a second substrate parallel to the transparent first substrate; a plurality of organic light emitting diodes (OLEDs) which are disposed on a surface of the second substrate to face the transparent first substrate and are electrically separated from each other; and a photo detector above the transparent first substrate that receives light emitted from a specimen, wherein the specimen is disposed on a surface of the transparent first substrate that does not face the second substrate.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
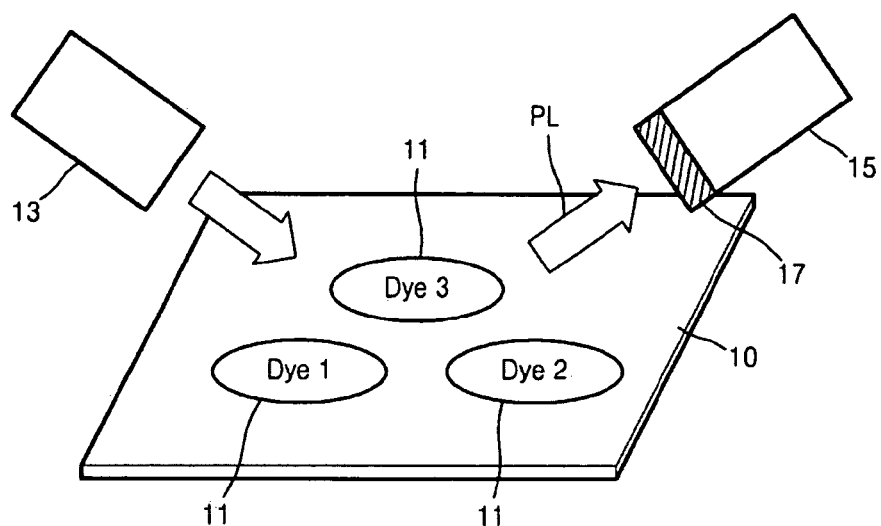
FIG. 1 is a schematic drawing of a conventional biosensor.

The present invention will now be described more fully with reference to the accompanying drawings in which exemplary embodiments of the invention are shown. In the drawings, the thicknesses of layers and regions are exaggerated for clarity.

Figure 2:
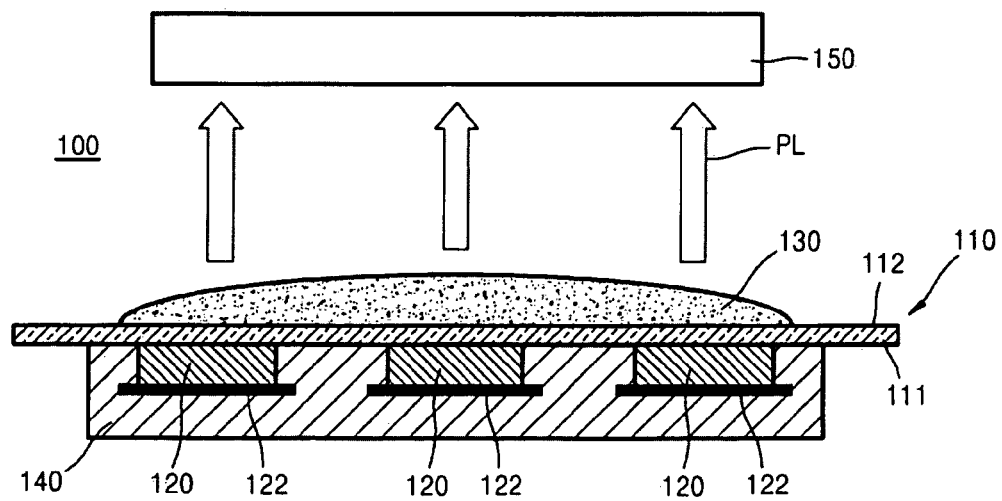
FIG. 2 is a cross-sectional view of a biosensor according to an embodiment of the present invention.

FIG. 2 is a cross-sectional view of a biosensor 100 according to an embodiment of the present invention. Referring to FIG. 2, a plurality of light sources 120 are formed on a first surface 111 of a transparent substrate 110. A specimen 130 is dropped on a region of a second surface 112 of the transparent substrate 110 to correspond to the light sources 120. The specimen 130 can be a DNA specimen or protein. The transparent substrate 110 can be formed of glass or plastic.

The light sources 120 may be organic light emitting diodes (OLEDs). The OLEDs 120 are connected to wires (not shown) and emit light using power externally supplied through the wire. The OLEDs 120 are eclectically separated from each other. A reflection film 122 is formed on a lower surface of each of the OLEDs 120. The reflection film 122 guides light emitted from the OLED 120 through the transparent substrate 110.

A sealing material 140 that protects the OLEDs 120 from air or moisture is formed on the first surface 111 of the transparent substrate 110. The sealing material 140 can be formed of a polymer resin or an epoxy resin.

A photo detector 150 is formed above the transparent substrate 110 to detect photo-luminance (PL) generated from a dye (not shown) included in the specimen when light is radiated to the dye. The photo detector 150 may be a photo diode. The photo detector 150 can be disposed above the light sources 120 and the specimen 130, and can be formed of a single device.

Figure 3:
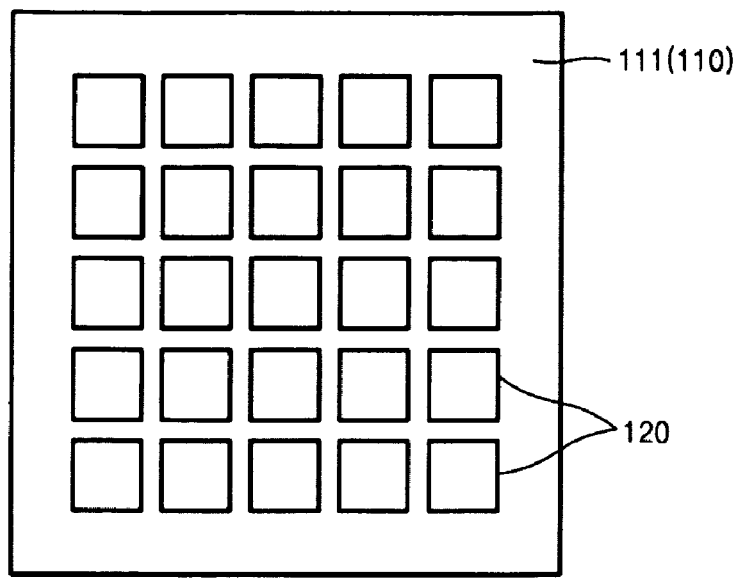
FIG. 3 is a plan view illustrating an arrangement of light sources according to an embodiment of the present invention.

FIG. 3 is a plan view illustrating an arrangement of light sources according to an embodiment of the present invention. Like reference numerals are used to denote elements that are substantially the same as elements of the biosensor 100 of FIG. 2.

Referring to FIG. 3, OLEDs 120 are disposed in a 5×5 matrix array on the first surface 111 of the transparent substrate 110. The OLEDs 120 can be manufactured in a micrometer scale using an inkjet printing or a shadow metal mask. Each of the OLEDs 120 can be formed in a single layer or in multiple layers that emit red, green or blue wavelength of light, respectively. The color control of the OLEDs 120 having desired spectrums can be independently formed according to the thickness of the OLEDs 120 and the degree of doping. Each of the material layers that constitute the OLED 120 may have a spectrum having a full width at half maximum of 50 to 100 nm.

Each of the OLEDs 120 can be independently switched ON. Thus, the twenty five light sources, that is, the OLEDs 120 can have light spectrums different from each other, and thus, it is possible to know in advance what kind of specific light spectrum will be emitted from each of the OLEDs 120 through the switching. Thus, the photo detector 150 can distinguish the PL generated with respect to the OLEDs 120 independently turned on without requiring the use of additional optical filters. The PL of a dye attached to the specimen 130, which is formed in a drop shape, can be measured by the photo detector 150 installed immediately above the specimen 130. In order to increase the sensitivity of the photo detector 150, a plurality of identical light sources 120 can be disposed on the transparent substrate 110 and turned on. Since a measuring time is very short, the life span of the OLEDs 120 may not a significant issue.

The biosensor 100 according to the present embodiment emits light having a predetermined spectrum by operating specific OLEDs 120, and PL is generated when a dye included in the specimen 130 receives the light from the OLED(S). At this point, the photo detector 150 detects a material included in the specimen 130 by detecting only the intensity of the light. Thus, since the biosensor 100 according to the present embodiment emits light having a specific spectrum that is already known, conventional optical filters that distinguish light of specific wavelengths in PL generated from the specimen 130 are unnecessary. Thus, the biosensor 100 can have an increased measuring sensitivity and have a compact structure.

In FIG. 3, the OLEDs 120 having a rectangular shape are shown, however, the shape of the OLEDs 120 according to the present invention is not limited thereto. The OLEDs 120 may have polygonal shapes.

Figure 4:
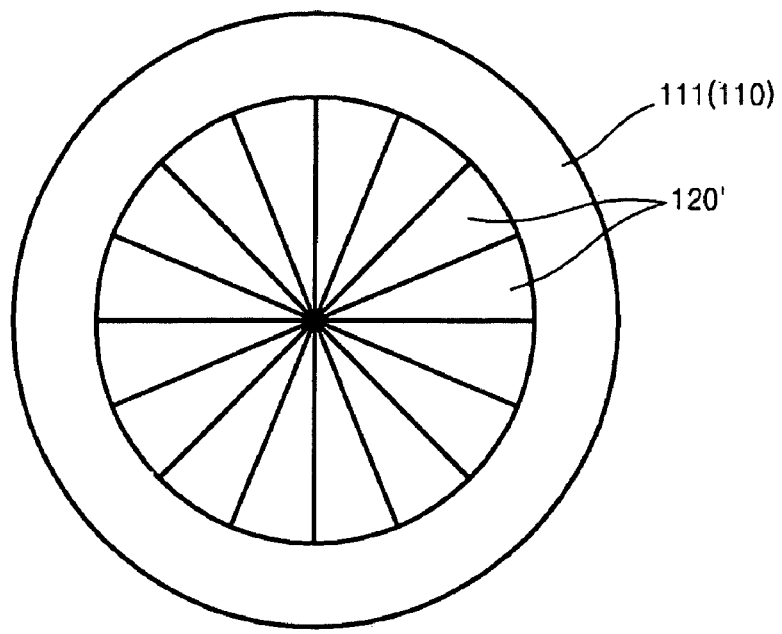
FIG. 4 is a plan view illustrating another arrangement of light sources according to an embodiment of the present invention.

FIG. 4 is a plan view illustrating another arrangement of light sources according to an embodiment of the present invention.

Referring to FIG. 4, a plurality of OLEDs 120', each being a segment of a circle, are formed on a first surface 111 of a transparent substrate 110. The OLEDs 120' can be formed using a shadow metal mask. The OLEDs 120' can be formed in a single layer or multiple layers of layers that emit red, green, or blue wavelength of light, respectively. The shapes and color control of the OLEDs 120' having desired spectrums can be independently formed according to the thickness of the OLEDs 120' and the degree of doping. Each of the OLEDs 120' can be independently switched ON. Thus, the light sources 120' can have light spectrums different from each other, and thus, it is possible to know in advance what kind of specific light spectrum will be emitted from each of the OLEDs 120' through the switching. Thus, PL generated with respect to the OLEDs 120' independently turned on can be distinguished without requiring the use of additional optical filters.

Figure 5:
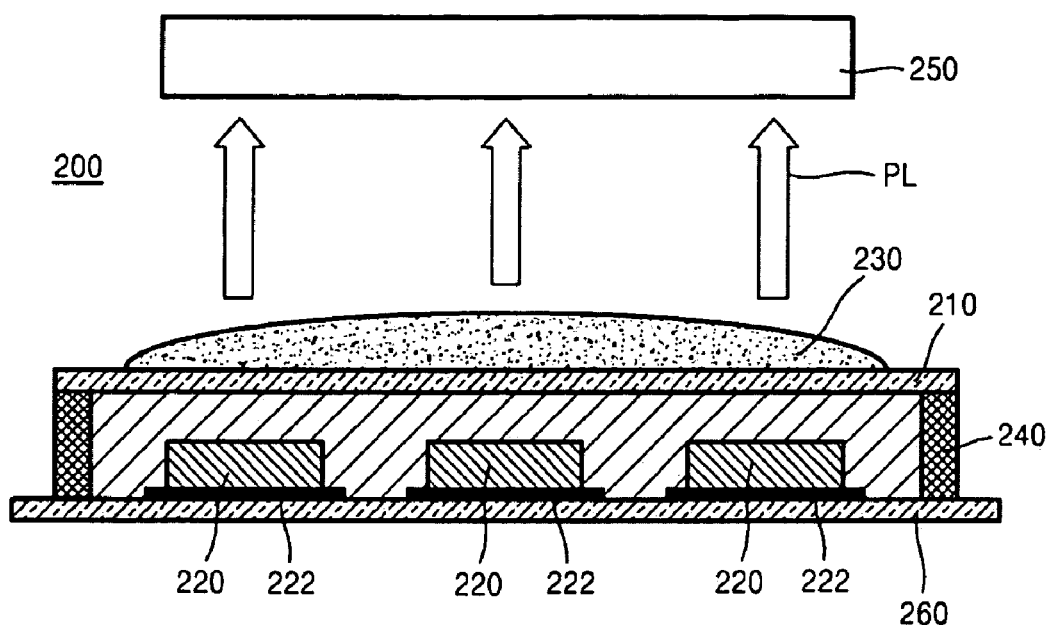
FIG. 5 is a cross-sectional view of a biosensor according to another embodiment of the present invention.

FIG. 5 is a cross-sectional view of a biosensor 200 according to another embodiment of the present invention. Referring to FIG. 5, a transparent first substrate 210 and a second substrate 260 are disposed parallel to each other, and a plurality of light sources 220 are disposed on a surface of the second substrate 260 facing the first transparent substrate 210. A specimen 230 is dropped on a region of the surface of the transparent first substrate 210 that corresponds to the light sources 220 and does not face the second substrate 260.

The light sources 220 can be OLEDs. The OLEDs 220 are connected to wires (not shown) and emit light by using externally supplied power through the wire. A reflection film 222 is installed on a lower-surface of each of the OLEDs 220. The reflection film 222 guides light emitted from the OLEDs 220 towards the transparent first substrate 210.

A sealing wall 240 is installed between the transparent first substrate 210 and the second substrate 260 to seal a space between the transparent first substrate 210 and the second substrate 260. A sealing material 242, such as polymer resin or epoxy resin, is filled inside the space.

A photo detector 250 that detects PL generated from the specimen 230 is installed above the transparent first substrate 210. The photo detector 250 may employ photo diodes.

The dispositions, shapes, and characteristics of the OLEDs 220 may be identical to the OLEDs 120 and 120', and the operation of the biosensor 200 is the same as the biosensor 100, and thus, the descriptions thereof will not be repeated.

As described above, in the biosensor that uses multiple light sources according to the present invention, optical filters are not disposed in a light receiving unit and the light sources and a specimen are disposed on either side of a transparent substrate. Thus, the biosensor has increased sensitivity, can be formed in a compact size, and can be manufactured at low cost.

A plurality of OLEDs as light sources can be easily formed on a substrate, and thus, one biosensor can measure many kinds of specimens.

The biosensor does not use optical filters, and when the multiple light sources are used as a single light source, the sensitivity of the biosensor can be increased.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A biosensor comprising:
a transparent substrate;
a plurality of organic light emitting diodes (OLEDs) which are disposed on a first surface of the transparent substrate and are electrically separated from each other, wherein each of the plurality of OLEDs emits light having a different wavelength from the remaining OLEDs of the plurality of OLEDs; and
a photo detector disposed above the transparent substrate, wherein the photo detector receives photoluminescence emitted from a specimen in response to irradiation via light from the plurality of OLEDs, and wherein the specimen is disposed on a second surface of the transparent substrate, the second surface being disposed substantially opposite to the first surface,
wherein the specimen is disposed on a region of the second surface of the transparent substrate.

2. The biosensor of claim 1, further comprising a plurality of reflection films, each formed on a surface of each of the plurality of OLEDs which do not face the transparent substrate.

3. The biosensor of claim 1, wherein the plurality of OLEDs are formed in a single layer or in multiple layers formed of a material that emits red, green, or blue wavelengths of light, respectively.

4. The biosensor of claim 3, wherein the material has a spectrum having a full width at half maximum of about 50 nm to about 100 nm.

5. The biosensor of claim 1, wherein the plurality of OLEDs are formed in a matrix arrangement.

6. The biosensor of claim 1, wherein each of the plurality of OLEDs has a shape of a segment of a circle, and at least two corresponding OLEDs together have corresponding shapes such that together the at least two corresponding OLEDs form a circle.

7. The biosensor of claim 1, wherein the plurality of OLEDs have a polygonal shape.

8. The biosensor of claim 1, further comprising a sealing material which covers the plurality of OLEDs on the transparent substrate.

9. A biosensor comprising:
a transparent first substrate;
a second substrate disposed substantially parallel to the transparent first substrate;
a plurality of organic light emitting diodes (OLEDs) which are disposed on a surface of the second substrate to face the transparent first substrate and which are electrically separated from each other, wherein each of the plurality of OLEDs emits light having a different wavelength from the remaining OLEDs of the plurality of OLEDs; and
a photo detector disposed above the transparent first substrate which receives photoluminescence emitted from a specimen in response to irradiation via light from the plurality of OLEDs, and wherein the specimen is disposed on a first surface of the transparent first substrate,
wherein the specimen is disposed on the first surface of the transparent first substrate that does not face the second substrate.

10. The biosensor of claim 9, further comprising a reflection film formed between the OLEDs and the second substrate.

11. The biosensor of claim 9, wherein the plurality of OLEDs are formed in a single layer or in multiple layers formed of a material that emits red, green, or blue wavelengths of light, respectively.

12. The biosensor of claim 10, wherein the material has a spectrum having a full width at half maximum of about 50 nm to about 100 nm.

13. The biosensor of claim 9, wherein the plurality of OLEDs are formed in a matrix arrangement.

14. The biosensor of claim 9, wherein each of the plurality of OLEDs has a shape of a segment of a circle, and at least two corresponding OLEDs together have corresponding shapes such that together the at least two corresponding OLEDs form a circle.

15. The biosensor of claim 9, wherein the plurality of OLEDs have a polygonal shape.

16. The biosensor of claim 9, further comprising a sealing material which fills a space between the transparent first substrate and the second substrate.

* * * * *